(12) United States Patent
Vuorenmaa et al.

(10) Patent No.: US 9,907,771 B2
(45) Date of Patent: *Mar. 6, 2018

(54) SAPONIFIED TALL OIL FATTY ACID FOR USE IN TREATMENT AND ANIMAL FEED SUPPLEMENTS AND COMPOSITIONS

(71) Applicant: Hankkija Oy, Hyvinkaa (FI)

(72) Inventors: Juhani Vuorenmaa, Hyvinkaa (FI); Hannele Kettunen, Tervakoski (FI)

(73) Assignee: Hankkija Oy, Hyvinkaa (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/371,442

(22) Filed: Dec. 7, 2016

(65) Prior Publication Data

US 2017/0079944 A1 Mar. 23, 2017

Related U.S. Application Data

(62) Division of application No. 14/401,242, filed as application No. PCT/FI2013/050518 on May 14, 2013, now abandoned.

(30) Foreign Application Priority Data

May 14, 2012 (FI) ..................................... 20125509

(51) Int. Cl.
  *A61K 36/13* (2006.01)
  *A61K 31/20* (2006.01)
  *A61K 31/19* (2006.01)
  *A61K 36/15* (2006.01)
  *A23K 20/158* (2016.01)
  *A23K 50/10* (2016.01)
  *A23K 50/15* (2016.01)
  *A23L 33/12* (2016.01)
  *A23K 50/75* (2016.01)
  *A61K 9/00* (2006.01)

(52) U.S. Cl.
  CPC ............ *A61K 31/20* (2013.01); *A23K 20/158* (2016.05); *A23K 50/10* (2016.05); *A23K 50/15* (2016.05); *A23K 50/75* (2016.05); *A23L 33/12* (2016.08); *A61K 9/0056* (2013.01); *A61K 31/19* (2013.01); *A61K 36/13* (2013.01); *A61K 36/15* (2013.01); *A23V 2002/00* (2013.01); *Y02P 60/56* (2015.11)

(58) Field of Classification Search
  CPC ..................................................... A61K 31/20
  See application file for complete search history.

(56) References Cited

U.S. PATENT DOCUMENTS

| 2,240,365 A | 4/1941 | Dreger |
| 2,308,431 A | 1/1943 | Brandt |
| 2,423,236 A | 7/1947 | Harwood et al. |
| 2,481,356 A | 9/1949 | Segessemann et al. |
| 2,530,810 A | 11/1950 | Christenson et al. |
| 2,611,706 A | 9/1952 | Bermhart et al. |
| 2,736,663 A | 2/1956 | Weber |
| 2,854,420 A | 9/1958 | Clark et al. |
| 2,866,739 A | 12/1958 | Ciesielski et al. |
| 2,894,939 A | 7/1959 | Hampton |
| 2,941,941 A | 6/1960 | Groll |
| 2,987,183 A | 6/1961 | Bishop |
| 3,001,962 A | 9/1961 | Carlston |
| 3,009,820 A | 11/1962 | Gould |
| 3,066,160 A | 11/1962 | Hampton |
| 3,141,897 A | 7/1964 | Crecelius et al. |
| 3,175,916 A | 3/1965 | Costigliola et al. |
| 3,194,728 A | 7/1965 | Stump, Jr. |
| 3,257,438 A | 6/1966 | Wicke et al. |
| 3,311,561 A | 3/1967 | Anderson et al. |
| 3,458,625 A | 7/1969 | Ensor et al. |
| 3,691,211 A | 4/1972 | Julian |
| 3,830,789 A | 8/1974 | Garrett et al. |
| 3,887,537 A | 6/1975 | Harada et al. |
| 3,926,936 A | 12/1975 | Lehtinen |
| 4,000,271 A | 12/1976 | Kremer et al. |
| 4,076,700 A | 2/1978 | Harada et al. |
| 4,118,407 A | 10/1978 | Red et al. |
| 4,313,940 A | 2/1982 | Pasarela |
| 4,437,894 A | 3/1984 | Emerson |
| 4,443,437 A | 4/1984 | Prokosch et al. |
| 4,810,299 A | 3/1989 | Schilling et al. |
| 4,810,534 A | 3/1989 | Seaborne et al. |
| 5,428,072 A | 6/1995 | Cook et al. |
| 5,460,648 A | 10/1995 | Walloch et al. |
| 6,020,377 A | 2/2000 | O'Quinn et al. |
| 6,229,031 B1 | 5/2001 | Strohmaier et al. |
| 6,608,222 B2 | 8/2003 | Bonsignore et al. |
| 8,741,171 B2 | 6/2014 | Swift et al. |
| 9,358,218 B2 | 6/2016 | Vourenmaa et al. |
| 9,422,507 B2 | 8/2016 | Hamunen |
| 2002/0147356 A1 | 10/2002 | Bonsignore et al. |
| 2002/0183298 A1 | 12/2002 | Schersl et al. |
| 2003/0144536 A1 | 7/2003 | Sonnier et al. |
| 2005/0107582 A1 | 5/2005 | Wong |

(Continued)

FOREIGN PATENT DOCUMENTS

| CA | 2 107 647 A1 | 4/1994 |
| CN | 101461443 A | 6/2009 |

(Continued)

OTHER PUBLICATIONS

European Search Report for European Patent Application No. 14797471.1 dated Dec. 6, 2016, 11 pgs.

(Continued)

*Primary Examiner* — Albert M Navarro
(74) *Attorney, Agent, or Firm* — Merchant & Gould P.C.

(57) ABSTRACT

The present invention relates to a tall oil fatty acid which is modified by saponification for use in the prevention of growth of harmful bacteria in the animal digestive tract and/or in the prevention of intestinal disorders. The invention further relates to a feed supplement and a feed composition comprising tall oil fatty acid which is modified by saponification.

16 Claims, 4 Drawing Sheets

(56) References Cited

U.S. PATENT DOCUMENTS

| | | |
|---|---|---|
| 2005/0203279 A1 | 9/2005 | Rojas et al. |
| 2006/0021276 A1 | 2/2006 | Sonnier |
| 2006/0286185 A1 | 12/2006 | Prokosch |
| 2008/0262251 A1 | 10/2008 | Sato et al. |
| 2009/0012164 A1 | 1/2009 | Kelderman |
| 2009/0220638 A1 | 9/2009 | Perez |
| 2009/0277972 A1 | 11/2009 | Kennon et al. |
| 2009/0285931 A1 | 11/2009 | Shelby et al. |
| 2009/0297687 A1 | 12/2009 | Ramirez et al. |
| 2011/0081442 A1 | 4/2011 | Weill et al. |
| 2011/0200570 A1 | 8/2011 | Mosbaugh et al. |
| 2011/0212217 A1 | 9/2011 | Herranen et al. |
| 2011/0212218 A1 | 9/2011 | Herranen et al. |
| 2012/0070516 A1 | 3/2012 | Tranquil et al. |
| 2013/0041192 A1 | 2/2013 | Saviainen et al. |
| 2015/0164966 A1 | 6/2015 | Vuorenmaa et al. |
| 2015/0238454 A1 | 8/2015 | Vuorenmaa et al. |
| 2016/0081368 A1 | 3/2016 | Vuorenmaa et al. |
| 2016/0081952 A1 | 3/2016 | Vuorenmaa et al. |
| 2016/0089407 A1 | 3/2016 | Vuorenmaa et al. |
| 2016/0250171 A1 | 9/2016 | Vuorenmaa et al. |
| 2016/0250269 A1 | 9/2016 | Rintola et al. |

FOREIGN PATENT DOCUMENTS

| | | |
|---|---|---|
| DE | 101 06 078 A1 | 9/2002 |
| EP | 0 078 152 A1 | 5/1983 |
| EP | 0 146 738 A2 | 7/1985 |
| EP | 1 586 624 A1 | 10/2005 |
| EP | 2 243 061 A1 | 7/2011 |
| FI | 41337 B | 6/1969 |
| FI | 20110371 A | 4/2013 |
| FI | 20120287 A | 4/2013 |
| GB | 955 316 A | 4/1964 |
| GB | 2 139 868 A | 11/1984 |
| GB | 2 271 282 A | 4/1994 |
| JP | S60-237008 A | 11/1985 |
| WO | WO 94/16690 A1 | 8/1994 |
| WO | WO 99/10148 A1 | 3/1999 |
| WO | WO 02/02106 A1 | 1/2002 |
| WO | WO 03/024681 A1 | 3/2003 |
| WO | WO 2006/040537 A1 | 4/2006 |
| WO | WO 2008/099051 A2 | 8/2008 |
| WO | WO 2008/154522 A1 | 12/2008 |
| WO | WO 2009/079680 A1 | 7/2009 |
| WO | WO 2009/106696 A1 | 9/2009 |
| WO | WO 2011/042613 A2 | 4/2011 |
| WO | WO 2011/055018 A2 | 5/2011 |
| WO | WO 2011/080399 A1 | 7/2011 |
| WO | WO 2011/099000 A2 | 8/2011 |
| WO | WO 2012/037297 A1 | 2/2012 |
| WO | WO 2013/060936 A1 | 5/2013 |
| WO | WO 2013/118099 A1 | 8/2013 |
| WO | WO 2013/171370 A1 | 11/2013 |
| WO | WO 2014/184430 A1 | 11/2014 |

OTHER PUBLICATIONS

European Search Report for European Patent Application No. 14797745.8 dated Dec. 5, 2016, 9 pgs.

European Search Report for European Patent Application No. 14797238.4 dated Dec. 7, 2016, 10 pgs.

Duncan, D.P., "Tall Oil Fatty Acids", *Naval Stores*, 346-349 (1989).

Gudmundur, B. et al., "Antibacterial, Antiviril and Antifungal Activities of Lipids" in "Lipids and Essential Oils as Antimicrobial Agents", *John Wiley & Sons*, 47-80 (2011).

Van Nevel, C. J. et al., "Effect of Fatty Acid Derivatives on Rumen Methane and Propionate in Vitro [1]", *Applied Microbiology*, 365-366 (1971).

Huwig, A. et al., "Mycotoxin detoxication of animal feed by different adsorbents", *Toxicology Letters*, 122: 179-188(2001).

Magee, T. et al., "Composition of American Distilled Tall Oils", *JAOCS*, 69(4): 321-324 (1992).

Shetty, P. et al., "*Saccharomyces cerevisiae* and lactic acid bacteria as potential mycotoxin decontaminating agents", *Trends in Food Science & Technology*, 17: 48-55 (2006).

"Carboxylic Acids, Fatty Acids from Tall Oil", Kirk-Othmer Encyclopedia of Chemical Technology, Copyright 1999-2014 by John Wiley and Sons, Inc., 4 pgs.

International Search Report for corresponding International Patent Application No. PCT/FI2013/050518 dated Sep. 12, 2013.

Finnish Search Report for corresponding Finnish Patent Application No. 20125509 dated Feb. 26, 2013.

Extended European Search Report for corresponding European Patent Application No. 13790829.9 dated Oct. 5, 2015.

Antila, M. et al., "The fatty acids of tall oil and their ethyl and glyceryl esters as animal fodder ingredients, the chemical and physical properties of the fatty acid fraction and esters prepared from this fraction", *Journal ACTA Agricultureae Scandinavia*, 12: 95-105, 1962, Abstract.

Bannink, A. et al., "A model of enteric fermentation in dairy cows to estimate methane emission for the Dutch National Inventory Report using the IPCC Tier 3 approach", 166-167: 603-618, 2011.

Beauchemic, K.A., et al., "Nutritional management for enteric methane abatement: a review", *Australian Journal of Experimental Agriculture*, 48: 21-27, 2008.

de Graaf et al., "Consumption of tall oil-derived phytosterols in a chocolate matrix significantly decreases plasma total and low-density lipoprotein-cholesterol levels", *British Journal of Nutrition*, 88: 479-488, 2002.

Grainger, C. et al., "Can enteric methane emissions from ruminants be lowered without lowering their production?", *Animal Feed Science and Technology*, 166-167: 308-320, 2011.

Machmüller, A., "Medium-chain fatty acids and their potential to reduce methanogenesis in domestic ruminants", *Agriculture, Ecosystems and Environment*, 112: 107-114, 2006.

Machmüller, A. et al., "Potential of various fatty feeds to reduce methane release from rumen fermentation in vitro (Rusitec)", *Animal Feed Science Technology*, 71: 117-130, 1998.

McGuire, J. et al., "Gas Chromatographic Analysis of Tall Oil Fractionation Products After Methylation with N, ,N-Dimethylformamide Dimethylacetal", *Journal of Chromatographic Science*, 36: 104-108, 1998.

Norlin, L. "Tall Oil", *Ullmann's Encyclopedia of Industrial Chemistry*, published online: Jun. 15, 2000.

O'Quinn, P.R. et al., "Effects of modified tall oil and creatine monohydrate on growth performance, carcass characteristics, and meat quality of growing-finishing pigs", *Journal of Animal Science*, 78(9): 2376-2382, 2000.

O'Quinn, P.R. et al., "Effects of modified tall oil versus a commercial source of conjugated linoleic acid and increasing levels of modified tall oil on growth performance and carcass characteristics of growing-finishing pigs", *Journal of Animal Science*, 78(9): 2359-2368, 2000.

O'Quinn, P.R. et al., "Effects of modified tall oil versus conjugated linoleic acid on finishing pig growth performance and carcass characteristics", *KSU Swine Day*, 157-161, 1998.

Patra, A.K., "Effects of Essential Oils on Rumen Fermentation, Microbial Ecology and Ruminant Production", *Asian Journal of Animal and Veterinary Advances*, 6(5): 416-428, 2011.

Polan, C.E. et al., "Biohydrogenation of Unsaturated Fatty Acids by Rumen Bacteria", *Journal of Bacteriology*, 88(4): 1056-1064, 1964.

Product Data Sheet SYLFAT® 2LTC tall oil fatty acid [online], Arizona Chemical, [last modified Jul. 20, 2009], retrieved Feb. 20, 2013, URL: http://www.arizonachemical.com/Global/PDS/EU_product_data_sheets/SYLFAT%C2%AE%202LTC.pdf.

Savluchinske-Feio, S. et al., "Antimicrobial activity of resin acid derivatives", *Applied microbiology and Biotechnology*, 72(3): 430-436, 2006.

Smith, E., et al., "Isopimaric Acid from *Pinus nigra* shows Activity against Multi-drug-resistant and EMRSA Strains for *Staphylococcus aureus*", *Phytotherapy Research*, 19(6): 538-542, 2005.

Snell, F. et al., "Comparative Value of Fatty Acids and Resin Acids of Tall Oil in Soaps", *The Journal of the American Oil Chemist's Society*, 27(8): 289-295, 1950.

(56) References Cited

OTHER PUBLICATIONS

Zhou, X. et al., "The Effect of Saturated Fatty Acids on Methanogenesis and Cell Viability of *Methanobrevibacter ruminantium*", *Archaea*, 2013: 1-9, 2013.
"Explanatory Notes to the Harmonized Commodity Description and Coding System", The Department of Duty Collection of the General Administration of Customs, China Commerce and TradePress, published on Jan. 31, 2007, see p. 478: "Tall Oil, Whether or Not Refined". English translation of relevant parts.

SAPONIFIED TALL OIL FATTY ACID FOR USE IN TREATMENT AND ANIMAL FEED SUPPLEMENTS AND COMPOSITIONS

This application is a Divisional of U.S. Ser. No. 14/401,242, filed 14 Nov. 2014, which is a National Stage Application of PCT/FI2013/050518, filed 14 May 2013, which claims benefit of Serial No. 20125509, filed 14 May 2012 in Finland and which applications are incorporated herein by reference. To the extent appropriate, a claim of priority is made to each of the above disclosed applications.

The invention relates to a modified tall oil fatty acid which is modified by saponification, use thereof, and feed supplement and feed composition comprising said modified tall oil fatty acid.

BACKGROUND OF THE INVENTION

Imbalances in microbial populations and growth of harmful bacteria in the digestive tract of animals can cause significant losses in animal growth and production. These imbalances manifest themselves as intestinal disorders such as diarrhea. While microbial infections of animals have been prevented by the use of e.g. antibiotics and other agents that prevent the growth of microorganisms, stricter regulations on their use are expected. Generally, there is an increasing demand for ingredients for use in animal feeding that can modulate the microbial population in the animal digestive tract but which are readily available, well tolerated and environmentally friendly.

Fractional distillation of crude tall oil, obtained as a by-product of the Kraft process of wood pulp manufacture, produces distilled tall oil (DTO) which typically comprises over 10% resin acids and less than 90% fatty acids. Further refinement of distilled tall oil produces tall oil fatty acid (TOFA), which is available in a variety of compositions differing in the fatty acids and resin acids content. Because TOFA is an inexpensive source of fatty acids, it has previously been used in animal nutrition as an energy source. For instance, GB 955316 discloses the use of alkali metal salts of tall oil fatty acids to improve weight gain and nitrogen retention in ruminant animals.

PURPOSE OF THE INVENTION

The purpose of the invention is to provide a new type of modified tall oil fatty acid/feed supplement for use in the prevention of growth of harmful bacteria in the animal digestive tract and/or in the prevention of intestinal disorders.

The present inventors have surprisingly found that saponification of TOFA improves the solubility of its components and resin acids in the digestive tract of an animal in particular and significantly increases its effectiveness in the prevention of growth of harmful bacteria in the animal digestive tract, in the modulation of microbial population of the animal digestive tract and/or in the prevention of intestinal disorders.

SUMMARY

A method for reducing harmful bacteria in an animal digestive tract and/or reducing intestinal disorders in the animal is provided. The method includes administering to the animal a tall oil fatty acid modified by saponification and comprising resin acids, and wherein the tall oil fatty acid comprises 90 to 98% (w/w) fatty acids.

A method for reducing harmful bacteria in an animal digestive tract and/or reducing intestinal disorders in the animal is provided. The method includes administering to the animal a feed supplement comprising a tall oil fatty acid modified by saponification and comprising resin acids, and wherein the tall oil fatty acid comprises 90 to 98% (w/w) fatty acids.

A method for reducing harmful bacteria in an animal digestive tract and/or reducing intestinal disorders in the animal is provided. The method includes administering to the animal a feed composition comprising a feed supplement comprising a tall oil fatty acid modified by saponification, the tall oil fatty acid comprising resin acids, and wherein the tall oil fatty acid comprises 90 to 98% (w/w) fatty acids.

DETAILED DESCRIPTION OF THE INVENTION

Figure 1A:
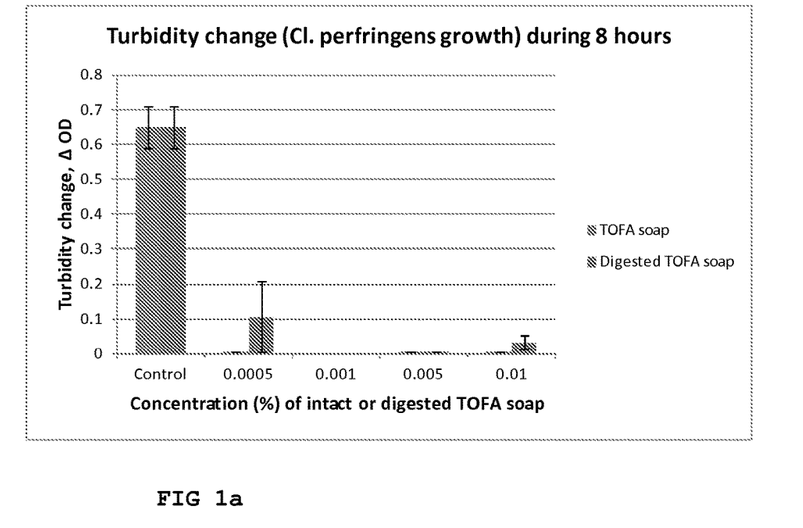
FIG. 1a The turbidity change during 8 hours of *Cl. perfringens* growth as a response to saponified TOFA and digested saponified TOFA concentrations 1.
Figure 1B:
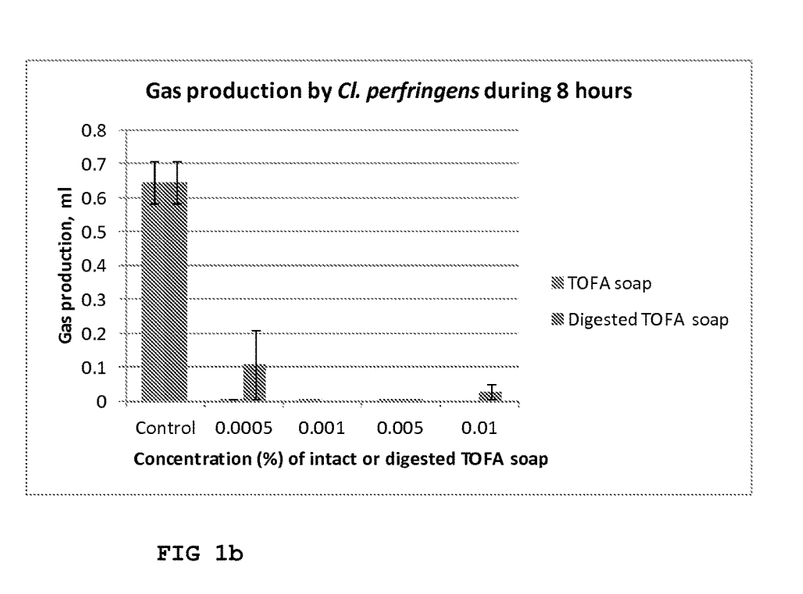
FIG. 1b Gas production during 8 hours by *Cl. perfringens* growth as a response to saponified TOFA and digested saponified TOFA concentrations.
Figure 2A:
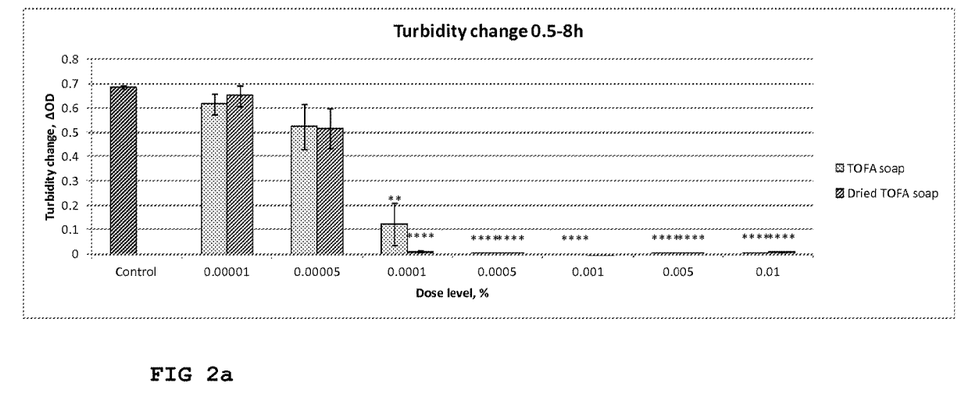
FIG. 2a The turbidity change during 8 hours of *Cl. perfringens* growth as a response to saponified TOFA and dried saponified TOFA concentrations.
Figure 2B:
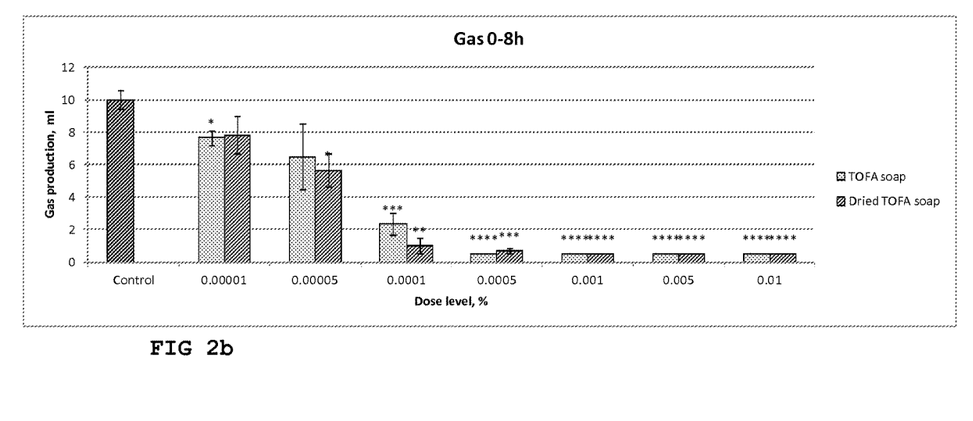
FIG. 2b Gas production during 8 hours by *Cl. perfringens* growth as a response to saponified TOFA and dried saponified TOFA concentrations.
Figure 3A:
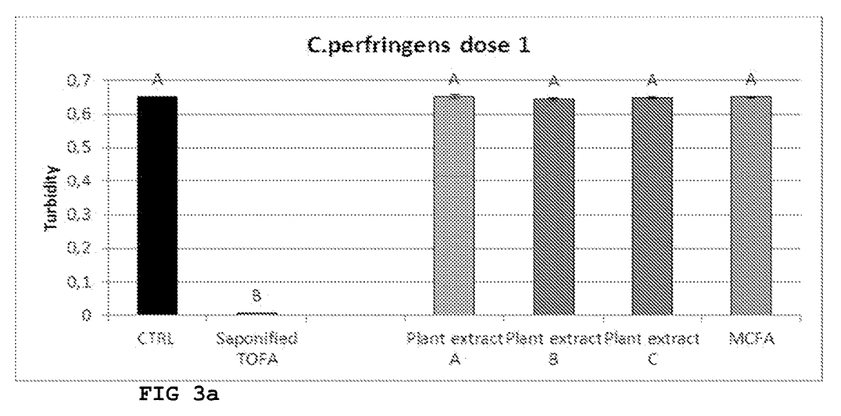
FIG. 3a The turbidity change during 8 hours of *Cl. perfringens* growth as a response to saponified TOFA and test products at dose 1.
Figure 3B:
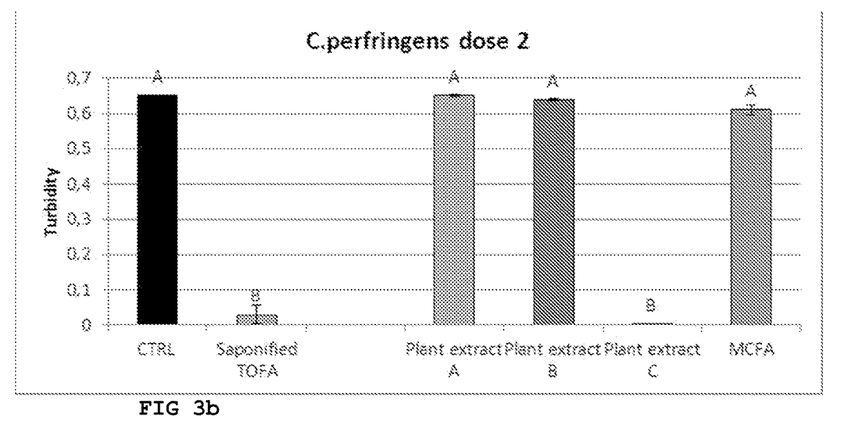
FIG. 3b The turbidity change during 8 hours of *Cl. perfringens* growth as a response to saponified TOFA and test products at dose 2.
Figure 3C:
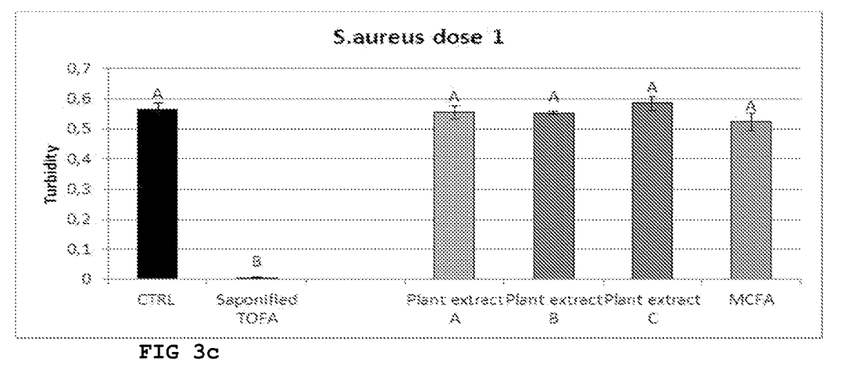
FIG. 3c The turbidity change during 8 hours of *S. aureus* as a response to saponified TOFA and test products at dose 1.
Figure 3D:
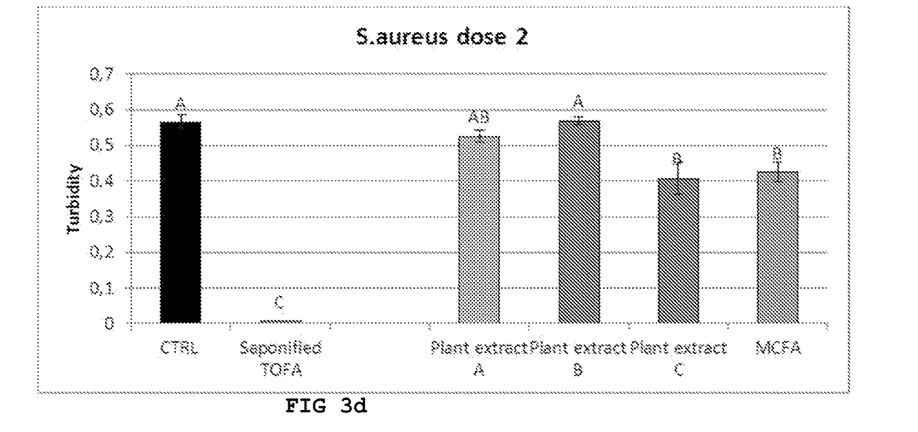
FIG. 3d The turbidity change during 8 hours of *S. aureus* as a response to saponified TOFA and test products at dose 2.
Figure 3E:
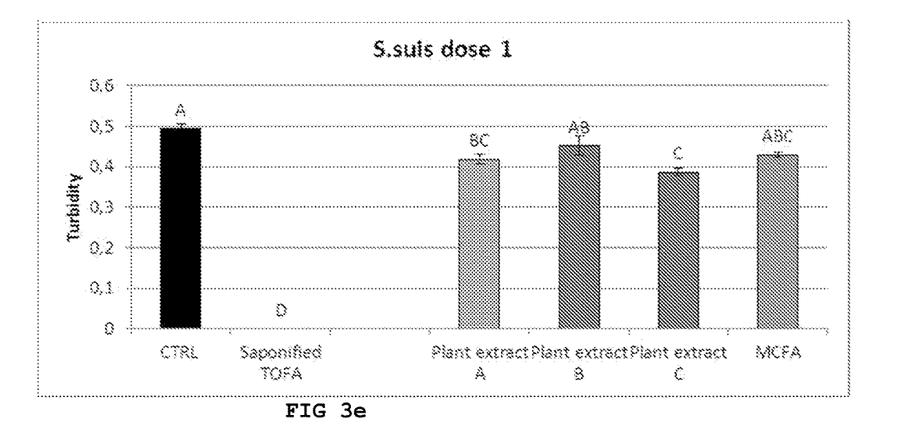
FIG. 3e The turbidity change during 8 hours of *S. suis* as a response to saponified TOFA and test products at dose 1.
Figure 3F:
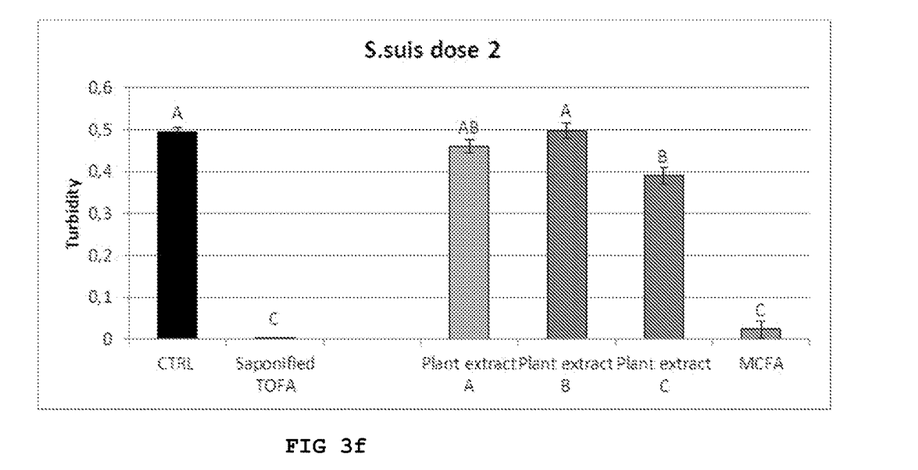
FIG. 3f The turbidity change during 8 hours of C *S. suis* as a response to saponified TOFA and test products at dose 2.

The present invention is based on the realization that tall oil fatty acid which is modified by saponification can be used in the prevention of growth of harmful bacteria in the animal digestive tract and/or in the prevention of intestinal disorders.

The term "tall oil fatty acid" or "TOFA" should be understood as referring to a composition obtained by distillation of crude tall oil and further refinement of distilled tall oil. TOFA or TOFA which is modified by saponification typically comprises 90-98% (w/w) fatty acids. Further, TOFA or TOFA which is modified by saponification may comprise 1-10% (w/w) resin acids.

Resin acids are known to have antimicrobial, including antibacterial, properties. However, the present inventors have found that resin acids of TOFA are poorly soluble in digestive juices and tend to precipitate in the digestive tract of an animal. Therefore their effectiveness in the digestive tract is less than optimal.

The modification of TOFA improves the solubility of its components and resin acids in the digestive tract of an animal.

In this context, the term "tall oil fatty acid which is modified by saponification" or "TOFA which is modified by saponification" should be understood as referring to TOFA that is chemically modified so as to improve the solubility of its components and resin acids in the digestive tract of an animal in particular.

In one embodiment of the present invention, the tall oil fatty acid which is modified by saponification for use according to the present invention comprises 1-10% (w/w) of resin acids.

In one embodiment of the present invention, TOFA or TOFA which is modified by saponification comprises 2-9% (w/w) resin acids.

In one embodiment of the present invention, TOFA or TOFA which is modified by saponification comprises 5-9% (w/w) resin acids.

In this context, the term "resin acids" should be understood as referring to a complex mixture of various acidic compounds comprised by tall oil which share the same basic skeleton including a three-fused ring. The exact composition of the resin acids present in TOFA varies e.g. according to the species of the trees the TOFA is obtained from and the processing conditions under which it is manufactured.

Resin acids typically include compounds such as abietic acid, dehydroabietic acid, levopimaric acid, neoabietic acid, pimaric acid and isopimaric acid, only to mention a few.

In one embodiment of the present invention, TOFA or TOFA which is modified by saponification comprises 90-98% (w/w) of fatty acids.

Various processes for the saponification of TOFA using e.g. NaOH or CaOH are known to a person skilled in the art.

In one embodiment of the present invention, the modified TOFA, the TOFA soap, for use according to the present invention is dried. The TOFA which is modified by saponification can be dried by spray drying, drum drying or by any other known suitable drying method.

The present invention also relates to a feed supplement comprising the tall oil fatty acid which is modified by saponification according to the invention.

In one embodiment of the present invention, the feed supplement is effective in the prevention of growth of harmful bacteria and/or for prevention of intestinal disorders.

In one embodiment of the present invention, the feed supplement comprises a tall oil fatty acid which is modified by saponification and which comprises 1-10% (w/w) resin acids.

In one embodiment of the present invention, the feed supplement comprises a tall oil fatty acid which is modified by saponification and which comprises 2-9% (w/w) resin acids.

In one embodiment of the present invention, the feed supplement comprises a tall oil fatty acid which is modified by saponification and which comprises 5-9% (w/w) resin acids.

In this context, the term "feed supplement" should be understood as referring to a composition that may be added to a feed or used as such in the feeding of animals. The feed supplement may comprise different active ingredients. The feed supplement may be added in the feed in a concentration of 0.0001-5 kg/ton of dry weight, preferably 0.005-1 kg/ton, most preferably 0.01-0.1 kg/ton of the dry weight of the total amount of the feed. The TOFA which is modified by saponification or the feed supplement comprising the TOFA which is modified by saponification according to the invention may be added to the feed or feed supplement as such, or it may in general be further processed as desired.

Further, the TOFA which is modified by saponification or the feed supplement comprising the TOFA which is modified by saponification according to the invention may be added to the feed or feed supplement, or it may be administered to an animal separately (i.e. not as a part of any feed composition).

In this context, the term "feed composition" or "feed" should be understood as referring to the total feed composition of an animal diet or to a part thereof, including e.g. supplemental feed, premixes and other feed compositions. The feed may comprise different active ingredients.

In one embodiment of the present invention, the feed supplement comprises TOFA which is modified by saponification and which is absorbed into a carrier material suitable for the feed composition such as sugarbeet pulp.

In one embodiment of the present invention, the feed supplement comprises TOFA which is modified by saponification and which is dried.

The present invention also relates to a feed composition comprising the feed supplement according to the invention.

In one embodiment of the present invention, the feed composition comprises the feed supplement in an amount of 0.00001-0.5% (w/w), preferably 0.0005-0.1% (w/w), most preferably 0.001-0.01% (w/w) of the dry weight of the total amount of the feed.

In one embodiment of the present invention, the feed composition comprises the feed supplement in the amount of 0.0005-0.1% (w/w) of the dry weight of the total amount of the feed.

The modified tall oil fatty acid or feed supplement according to the invention is produced by saponification. The method comprises the steps of adding a base to an aqueous TOFA solution and heating the mixture. The mixture is stirred during the heating step. The mixture is heated at a temperature of 80-120° C., preferably at 85-95° C., for a period of 1-3 hours, preferably for 2 hours.

Any base suitable for saponification, such as an alkali metal hydroxide, can be used as the base.

In one embodiment of the present invention, the base that is used is a sodium or potassium hydroxide.

In one embodiment of the present invention, the method of producing a saponified tall oil fatty acid or feed supplement further comprises a step of drying. The dying can be carried out by spray drying, drum drying or by any other known drying method.

The invention also relates to a method of preventing the growth of harmful bacteria in the animal digestive tract and/or preventing intestinal disorders, comprising the step of administering to an animal the tall oil fatty acid which is modified by saponification according to the invention.

In this context, the term "harmful bacteria" should be understood as referring to any bacteria that is capable of affecting the digestive tract or health of an animal in an adverse manner, including competition for nutrients with the host animal. (In this context, the term "microbial population" should be understood as referring to the microorganisms that inhabit the digestive tract, including the Bacteria and Archaea domains and microscopic members of the Eukaryote domain and also intestinal parasites. The microbial population will vary for different animal species depending on e.g. the health of an animal and on environmental factors.

In this context, the term "intestinal disorder" should be understood as referring to various disorders of the digestive tract in an animal, including e.g. diarrhea and other intestinal health problems.

In this context, the term "animal" should be understood as referring to all kinds of different animals, such as monogastric animals, ruminants, fur animals, pets and aquaculture. Non-limiting examples of different animals, including offspring, are cows, beef cattle, pigs, poultry, sheep, goats, horses, foxes, dogs, cats and fish.

In one embodiment of the present invention, the TOFA which is modified by saponification is administered to an animal in an effective amount. In a further embodiment, the TOFA which is modified by saponification is administered in a therapeutically effective amount.

The present invention has a number of advantages. TOFA is a readily available, natural, lowcost and environmentally friendly material. Further, it is non-toxic and well tolerated. Subsequently, other benefits of the invention are e.g. improved animal health and productivity, higher product quality, uniformity, food and product safety. The invention also allows the production of feed compositions and supplements at low cost.

The embodiments of the invention described hereinbefore may be used in any combination with each other. Several of the embodiments may be combined together to form a further embodiment of the invention.

A product, a method or a use, to which the invention is related, may comprise at least one of the embodiments of the invention described hereinbefore.

EXAMPLES

In the following, the present invention will be described in more detail.

Example 1

Pathogen Inhibition Test

*Clostridium perfringens* is a pathogenic bacterium that causes necrotic enteritis in broiler chicks and other species of poultry. This experiment was conducted to study the inhibition of *Cl. perfringens* by saponified TOFA with 5% resin acids.

The saponified TOFA was manufactured by adding 140 mg of NaOH (sodium hydroxide) to 1 gram of TOFA, adding enough water to adjust the total dry matter (TOFA) percentage of the mixture to 18-20%, heating the mixture to +90° C., keeping the temperature at +90° C. for 120 minutes, during which time the mixture was gently stirred at 15 min intervals.

The efficiency of untreated and digested test compounds was tested in a *Cl. perfringens* growth inhibition test that measures both the turbidity of the clostridial culture medium as a result of increased number of bacterial cells in a unit volume of medium, and the cumulative gas production during the simulation.

Preparations of TOFA with 5% resin acids were produced:

1. Saponified TOFA with 15% dry matter content
2. Saponified and digested TOFA

Gastrointestinal digestion of the saponified TOFA: Part of the saponified TOFA was digested by a pepsin-HCl treatment (pH 2.5) at +37° C. for 3 hours, followed by neutralization of the digesta with NaOH (pH 6.5) and the treatment with bile acids and pancreatin for additional 3 hours at +37° C. This digestion mimics the gastric and small-intestinal digestion of monogastric animals. The digestion was made to evaluate whether the products would resist the conditions of the upper gastrointestinal tract before they enter the distal intestine with higher microbial activity.

The efficiency of TOFA against the growth of *Cl. perfringens* was tested at five concentrations of the dry matter of TOFA: 0%, 0.05%, 0.01%, 0.005%, 0.001% and, 0.0005%. Each treatment-concentration combination was replicated three times.

Simulation procedure: The simulation was conducted in 25-ml glass bottles containing 15 ml of sterile anaerobic TSGY-media (tryptic soy broth—yeast extract media with glucose) and the bottles were enclosed with air-tight stoppers to ensure anaerobic conditions throughout the experiment. At the beginning of the simulation 0.1% inoculums of the overnight grown *Cl. perfringens* culture was injected to TSGY-bottles. Test compounds, or sterile deionized water for the control treatment, were added in a 150 μl final volume from the respective stock solution according to the treatment. The simulation bottles were randomized to avoid artificial bias between treatments. The bottles were kept at an even 37° C. temperature and mixed 1 min before the turbidity measurement at each time point. The total simulation time was 8 h.

The optical density was measured at the time points of 0.5, 3, 6 and 8 hours. The turbidity (optical density, OD) of growth media increases proportionally as the *Cl. perfringens* cell number and cell density increases.

The total gas production was measured at the end of the 8 h simulation as an indicator of growth efficiency, since *Cl. perfringens* produces gas due to the active metabolism during exponential growth.

The student's t-test was used to compare the control treatment without TOFA against the saponified TOFA and digested saponified TOFA, and the two TOFA treatments against each other.

Results

The results are illustrated in FIGS. 1*a* and 1*b*. The TOFA treatments very effectively and statistically significantly ($p<0.05$) inhibited the growth of *Cl. perfringens* down to the concentration of 0.0005%, which was detected as the lack of turbidity change (FIG. 1*a*) and the production of negligible amounts of gas (FIG. 1*b*). The concentration 0.05% of TOFA, which is not shown in the figures, totally prevented the growth of *Cl. perfringens*.

The results show that saponified TOFA resists gastrointestinal digestion and maintains its efficacy against the growth of *Cl. perfringens*. This result shows that the saponified TOFA prevents or alleviates the onset of necrotic enteritis if given to broiler chicks or other species of poultry in the feed.

The experiment shows that the saponified TOFA is very effective against the growth of *Cl. perfringens*, and that most of its activity can resist gastrointestinal digestion.

Example 2

Pathogen Inhibition Test

This experiment was conducted to study the inhibition of *Cl. perfringens* by saponified TOFA with 7% resin acids. The saponification of the TOFA was conducted as described in Example 1. The efficiency of liquid and spray-dried TOFA soap was tested in a *Cl. perfringens* growth inhibition test that measures both the turbidity of clostridial culture medium as a result of an increased number of bacterial cells in a unit volume of the medium, and the cumulative gas production during the simulation.

Preparations of TOFA with 7% resin acids:

1. Liquid TOFA with a 20.4% dry matter content
2. Spray dried saponified TOFA

The spray-dried saponified TOFA was tested in the present trial in order to study the resistance of the product to drying and to detect any possible loss of efficacy due to the spray drying.

The efficiency of TOFA against the growth of *Cl. perfringens* was tested at eight concentrations of the dry matter of TOFA: 0% (Control), 0.01%, 0.005%, 0.001% 0.0005%, 0.0001%, 0.00005% and 0.00001%. Each treatment-concentration combination was replicated three times.

The simulation procedure and optical density and gas production measurements were conducted similarly as in Example 1.

The student's t-test was used to compare the control treatment without TOFA against the saponified TOFA and spray-dried saponified TOFA, and the two TOFA treatments against each other. The student's t-test p-values correspond to: ~$p<0.1$; *$p<0.05$; $p<0.01$: *$p<0.001$; ****$p<0.0001$.

Results

The results are illustrated in FIGS. 2*a* and 2*b*. The TOFA treatments very effectively and statistically significantly ($p<0.01$) inhibited the growth of *Cl. perfringens* down to the concentration of 0.0001%, which was detected as the lack of turbidity change (FIG. 2*a*) and the production of negligible amounts of gas (FIG. 2*b*). The products at the concentrations of 0.00005% and 0.00001% had some inhibitory effect on the production of gas, indicating an anti-clostridial effect even at these low concentrations.

The results show that spray dried TOFA is as efficient against the growth of *Cl. perfringens* as liquid TOFA. Thus, the efficacy of the product is not impaired by spray drying. This result also shows that the saponified TOFA prevents or alleviates the onset of necrotic enteritis, if given to broiler chicks or other species of poultry in the feed.

This experiment suggests that the saponified TOFA is very effective against the growth of *Cl. perfringens*, as a liquid or spray dried product.

Example 3

Pathogen Inhibition Test

This experiment was conducted to compare the efficacy of saponified TOFA with 8.5% resin acids and competing products for their ability to inhibit the growth of pure cultures of three Gram-positive pathogens: *Clostridium perfringens, Staphylococcus aureus* and *Streptococcus suis* in vitro. The competing products were commercial natural plant extracts and a medium-chain fatty acid product. Plant extracts A-C are merchandised to have inhibitory effects against Gram+ pathogenic bacteria and they can be used e.g. in management of coccidiosis risk. The saponification of the TOFA was conducted as described in Example 1. Before the simulation, the bacteria were grown overnight as pure cultures in their specific growth medium. The bacterial cultures were used as inoculant in the experiment Products and product doses are presented in Table 1.

| Product | Dose 1 (kg/ton of feed) | Dose 2 (kg/ton of feed) |
|---|---|---|
| Saponified TOFA 8.5% resin acids | 0.25 | 0.50 |
| Plant (Oregano) extract A | 0.25 | 0.50 |
| Plant extract B | 0.25 | 0.50 |
| Plant extract C | 0.50 | 1.00 |
| Medium chain fatty acid product (MCFA) | 0.25 | 0.50 |

The test products were first weighed into the glass bottles. 15 ml of bacterial growth medium was added. Bottles for *Cl. perfringens* and *S. aureus* were prepared in anaerobic glove box, while the bottles for *S. suis* and *B. cereus* were prepared in aerobic environment. Next, the bottles were enclosed with air-tight stoppers to ensure anaerobic conditions throughout the experiment for *Cl. perfringens* and *S. aureus*. A needle was pushed through the stoppers of the two aerobic bacteria to ensure oxygen supply for the culture. 150 ml of bacterial culture was added into each bottle to act as an inoculum (1% of the volume). The simulation time was calculated starting from the time of inoculating each vessel. During the simulation, the bottles were kept at 37° C. temperature in a constant, slow shaking for eight hours. Optical density was measured at the time points of 0, 2, 4, 6 and 8 hours. The turbidity (optical density, OD) of growth media increases proportionally as bacterial cell density increases.

Each product was tested at two concentrations and three replicates per concentration. Dose 2 was the recommended dose of the commercial products. Each product concentration had also a control vessel into which microbes were not included (one replicate/product/dose). These treatments controlled for any potential increase in the cloudiness that the test products may have induced into the growth medium during the simulation time. The total number of simulation vessels was 123 per bacterial species.

Results

The results are illustrated in FIGS. 3*a* to 3*f*. The saponified TOFA of the invention totally inhibited the growth of *Cl. perfringens* at both product levels at the 8-hour time point (FIGS. 3*a* and 3*b*).

*S. aureus* was not able to grow at all in the presence of saponified TOFA at the studied concentrations, while the other products showed no inhibition at dose 1 (FIG. 3*c*). Two of the other products showed partial inhibition at product dose 2 (FIG. 3*d*).

Saponified TOFA fully prevented the growth of *Streptococcus suis* during the 8-hour simulation at both product doses (FIGS. 3*e* and 3*f*). At dose 2, MCFA product efficiently inhibited the growth of *S. suis* at the 8-hour time point (FIG. 3*f*).

The experiment shows that the saponified TOFA is much more effective against the growth of *Cl. perfringens, Staphylococcus aureus* and *Streptococcus suis* as the commercial plant extracts A-C and MCFA claiming inhibitory effects against Gram+ pathogenic bacteria.

It is obvious to a person skilled in the art that, with the advancement of technology, the basic idea of the invention may be implemented in various ways. The invention and its embodiments are thus not limited to the examples described above; instead they may vary within the scope of the claims.

The invention claimed is:

1. A method for reducing harmful bacteria in an animal digestive tract and/or reducing intestinal disorders in the animal, the method comprising:

administering to the animal a tall oil fatty acid modified by saponification and comprising resin acids, and wherein the tall oil fatty acid comprises 90 to 98% (w/w) fatty acids.

2. The method of claim 1, wherein the tall oil fatty acid comprises 1 to 10% (w/w) resin acids.

3. The method of claim 1, wherein the tall oil fatty acid comprises 2 to 9% (w/w) resin acids.

4. The method of claim 1, wherein the tall oil fatty acid comprises 5 to 9% (w/w) resin acids.

5. The method of claim 1, wherein the tall oil fatty acid comprises 91 to 98% (w/w) fatty acids.

6. The method of claim 1, wherein the tall oil fatty acid is dried.

7. A method for reducing harmful bacteria in an animal digestive tract and/or reducing intestinal disorders in the animal, the method comprising:

administering to the animal a feed supplement comprising a tall oil fatty acid modified by saponification and comprising resin acids, and wherein the tall oil fatty acid comprises 90 to 98% (w/w) fatty acids.

8. The method of claim 7, wherein the tall oil fatty acid comprises 1 to 10% (w/w) resin acids.

9. The method of claim 7, wherein the tall oil fatty acid comprises 2 to 9% (w/w) resin acids.

10. The method of claim 7, wherein the tall oil fatty acid comprises 5 to 9% (w/w) resin acids.

11. The method of claim 7, wherein the tall oil fatty acid is dried.

12. The method of claim 7, wherein the tall oil fatty acid is absorbed into a carrier material.

13. A method for reducing harmful bacteria in an animal digestive tract and/or reducing intestinal disorders in the animal, the method comprising:

administering to the animal a feed composition comprising a feed supplement comprising a tall oil fatty acid modified by saponification, the tall oil fatty acid comprising resin acids, and wherein the tall oil fatty acid comprises 90 to 98% (w/w) fatty acids.

14. The method of claim 13, wherein the feed composition comprises from 0.00001 to 0.5% (w/w) of the feed supplement based on dry weight of the feed composition.

15. The method of claim 13, wherein the feed composition comprises from 0.0005-0.1% (w/w) of the feed supplement based on dry weight of the feed composition.

16. The method of claim 13, wherein the feed composition comprises from 0.001-0.01% (w/w) of the feed supplement based on dry weight of the feed composition.

* * * * *